United States Patent [19]

Failli et al.

[11] Patent Number: 5,389,639

[45] Date of Patent: Feb. 14, 1995

[54] AMINO ALKANOIC ESTERS OF RAPAMYCIN

[75] Inventors: Amedeo A. Failli, Princeton Junction, N.J.; Robert J. Steffan, Langhorne, Pa.

[73] Assignee: American Home Products Company, Madison, N.J.

[21] Appl. No.: 174,120

[22] Filed: Dec. 29, 1993

[51] Int. Cl.[6] .................. A61K 31/445; C07D 487/04
[52] U.S. Cl. .................... 514/291; 540/456; 514/211
[58] Field of Search ............... 540/456; 514/291, 211

[56] References Cited

U.S. PATENT DOCUMENTS

| B1 5,120,842 | 6/1993 | Failli et al. | 540/452 |
| 3,929,992 | 12/1925 | Seghal et al. | 424/122 |
| 3,993,749 | 11/1976 | Seghal et al. | 424/122 |

(List continued on next page.)

FOREIGN PATENT DOCUMENTS 0507555 10/1992 European Pat. Off. ............ 540/456

OTHER PUBLICATIONS

Vezina et al "J. Antibiotics" vol. 28 pp. 721–726 (1975).
(List continued on next page.)

*Primary Examiner*—Robert T. Bond
*Attorney, Agent, or Firm*—Arnold S. Milowsky

[57] ABSTRACT

This invention provides a compound of the structure

[structure of rapamycin derivative with OR$^1$, OMe, OR$^2$, MeO, OMe, HO, N, O substituents; positions 42 and 31 labeled]

wherein R$^1$ and R$^2$ are each, independently, hydrogen or $$-\!\!\!-\!\!\overset{O}{\underset{}{C}}\!\!-\!(CH_2)_{\overline{m}}\!-\!\underset{R^3}{\overset{R^4}{\underset{|}{CH}}}\!-\!(CH_2)_{\overline{n}}\!-\!N\!\!\overline{\!-\!}_pR^5;$$

R$^3$ is —(CH$_2$)$_q$CO$_2$R$^6$;
R$^4$ is hydrogen, alkyl, or arylalkyl;
R$^5$ is hydrogen or COOR$^7$;
R$^6$ is hydrogen, alkyl, alkenyl, arylalkyl, fluorenylmethyl, or phenyl which is optionally substituted;
R$^7$ is alkyl, alkenyl, arylalkyl, fluorenylmethyl, or phenyl which is optionally substituted;
m is 0–4;
n is 0–4;
p is 1–2;
q is 0–4;

wherein R$^3$, R$^4$, m, and n are independent in each of the $$[\overset{O}{\underset{}{C}}\!\!-\!(CH_2)_{\overline{m}}\!-\!\underset{R^3}{\overset{R^4}{\underset{|}{CH}}}\!-\!(CH_2)_{\overline{n}}\!-\!N]$$

subunits when p=2;
with the proviso that R$^1$ and R$^2$ are not both hydrogen; and further provided that if R$^5$ is CO$_2$R$^7$, then R$^6$ is hydrogen; and still further provided that if R$^6$ is not hydrogen, then R$^5$ is hydrogen;
or a pharmaceutically acceptable salt thereof which is useful as an immunosuppressive, antiinflammatory, antifungal, antiproliferative, and antitumor agent.

14 Claims, No Drawings

U.S. PATENT DOCUMENTS

| | | | |
|---|---|---|---|
| 4,316,885 | 2/1982 | Rakhit | 546/90 |
| 4,375,464 | 3/1983 | Sehgal et al. | 424/122 |
| 4,401,653 | 8/1983 | Eng et al. | 424/122 |
| 4,650,803 | 3/1987 | Stella et al. | 546/456 |
| 4,885,171 | 12/1989 | Seghal et al. | 424/122 |
| 5,023,262 | 6/1991 | Caufield et al. | 540/456 |
| 5,023,263 | 6/1991 | Von Burg | 540/456 |
| 5,023,264 | 6/1991 | Caufield et al. | 514/291 |
| 5,078,999 | 1/1992 | Warner et al. | 424/122 |
| 5,080,899 | 1/1992 | Sturm | 424/122 |
| 5,091,389 | 2/1992 | Ondeyka et al. | 514/291 |
| 5,100,883 | 3/1992 | Schiehser | 514/183 |
| 5,100,899 | 3/1992 | Calne | 514/291 |
| 5,102,876 | 4/1992 | Caufield | 514/183 |
| 5,118,677 | 6/1992 | Caufield | 514/183 |
| 5,118,678 | 6/1982 | Kao et al. | 314/183 |
| 5,120,842 | 6/1992 | Failli et al. | 540/452 |
| 5,130,307 | 7/1992 | Failli et al. | 540/456 |
| 5,138,051 | 8/1992 | Hughes et al. | 540/456 |
| 5,151,413 | 9/1992 | Caufield et al. | 514/63 |
| 5,169,851 | 12/1992 | Hughes et al. | 514/291 |
| 5,177,203 | 1/1993 | Failli et al. | 540/456 |
| 5,194,447 | 3/1993 | Kao | 514/456 |
| 5,221,670 | 6/1993 | Caufield | 514/483 |
| 5,233,036 | 8/1993 | Hughes | 540/455 |
| 5,286,730 | 2/1994 | Caufield et al. | 514/291 |
| 5,286,731 | 2/1994 | Caufield et al. | 514/291 |

OTHER PUBLICATIONS

Sehgal et al "J. Antibiotics" vol. 28, pp. 723–732 (1975).
Baker et al. "J. Antibiotics" vol. 31 pp. 539–545 (1978).
Martel et al. "Can J. Physiol. Pharmacol" vol. 33, pp. 48–51 (1977).
Staruci et al "FASEB" vol. 3, No. 3 (1989) Item 3411.
Dumont et al "FASEB" vol. 3, No. 4 (1989) Item 5256.
Calne et al. "Lancet" (1978) pp. 1183–1185.
Morris et al "Med. Sci. Res." vol. 17 No. 14 pp. 609–610 (1989).
Stepkowski et al., "Transplantation Proceedings" vol. 23 pp. 507–508 (1991).
Sechal et al, vol. 121 Abstract 5th Int Conf of Inflammation Research Assoca (Sep. 1990).
J. Heart and Lung Transplantation vol. 11 p. 197 (1992) Gregory et al.

AMINO ALKANOIC ESTERS OF RAPAMYCIN

BACKGROUND OF THE INVENTION

This invention provides amino alkanoic esters of rapamycin and a method for using them for inducing immunosuppressive, and in the treatment of transplantation rejection, graft vs. host disease, autoimmune diseases, diseases of inflammation, solid tumors, fungal infections, and hyperproliferative vascular disorders.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis: and effectively inhibited the formation of IgE-like antibodies.

The immunosuppressive effects of rapamycin have been disclosed in FASEB 3, 3411 (1989) and its utility in preventing transplantation rejection shown in U.S. Pat. No. 5,100,899. Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)].

Rapamycin has also been shown to be useful in preventing or treating systemic lupus erythematosus [U.S. Pat. No. 5,078,999], pulmonary inflammation [U.S. Pat. No. 5,080,899], insulin dependent diabetes mellitus [Fifth Int. Conf. Inflamm. Res. Assoc. 121 (Abstract), (1990) and European Patent Application 507,555 A1], and smooth muscle cell proliferation and intimal thickening following vascular injury [Morris, R. J. Heart Lung Transplant 11 (pt. 2): 197 (1992)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42- positions. U.S. Pat. No. 5,130,307 discloses aminoesters of rapamycin useful as immunosuppressive, antiinflammatory and antifungal agents. U.S. Pat. No. 5,221,670 discloses esters of rapamycin useful as immunosuppressive, antiinflammatory, antitumor and antifungal agents.

DESCRIPTION OF THE INVENTION

This invention provides derivatives of rapamycin which are useful as immunosuppressive, antiinflammatory, antifungal, antiproliferative, and antitumor agents having the structure

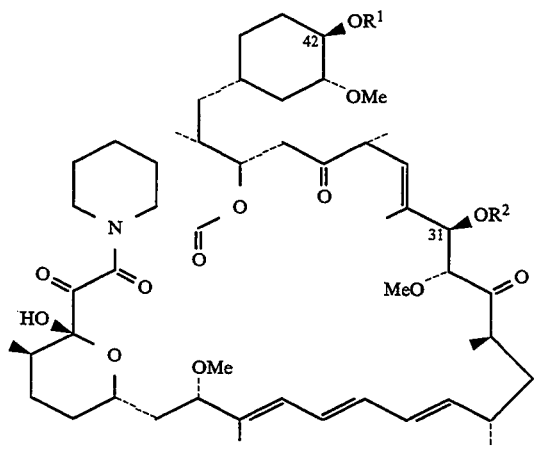

wherein $R^1$ and $R^2$ are each, independently, hydrogen or

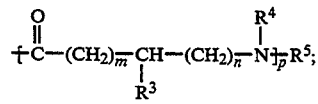

$R^3$ is $-(CH_2)_q CO_2 R^6$;
$R^4$ is hydrogen, alkyl of 1-6 carbon atoms, or arylalkyl of 7-10 carbon atoms;
$R^5$ is hydrogen or $COOR^7$;
$R^6$ is hydrogen, alkyl of 1-6 carbon atoms, alkenyl of 2-7 carbon atoms, arylalkyl of 7-10 carbon atoms, fluorenylmethyl, or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or $-CO_2H$;
$R^7$ is alkyl of 1-6 carbon atoms, alkenyl of 2-7 carbon atoms, arylalkyl of 7-10 carbon atoms, fluorenylmethyl, or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or $-CO_2H$;
m is 0–4;
n is 0–4;
p is 1–2;
q is 0–4;
wherein $R^3$, $R^4$, m, and n are independent in each of the

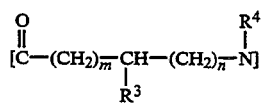

subunits when p=2;
with the proviso that $R^1$ and $R^2$ are not both hydrogen; and further provided that if $R^5$ is $CO_2R^7$, then $R^6$ is hydrogen; and still further provided that if $R^6$ is not hydrogen, then $R^5$ is hydrogen;
or a pharmaceutically acceptable salt thereof.

The pharmaceutically acceptable salts are those derived from such inorganic cations such as sodium, potassium and the like; organic bases such as: mono-, di-, and trialkylamines of 1-6 carbon atoms per alkyl group and mono-, di-, and trihydroxyalkylamines of 1-6 carbon atoms per alkyl group, and the like; and organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids. Based on this disclosure, other pharmaceutically acceptable salts that can be formed will be readily apparent to one skilled in the art.

It is preferred that the aryl moiety of the arylalkyl group is a phenyl, naphthyl, pyridinyl, quinolinyl, isoquinolinyl, thienyl, thionaphthyl, furanyl, benzofuranyl, benzodioxyl, benzoxazolyl, benzoisoxazolyl, indolyl, thiazolyl, isoxazolyl, pyrimidinyl, pyrazinyl, benzopyranyl, or benzimidazolyl group which may be optionally mono-, di-, or tri- substituted with a group selected from alkyl of 1-6 carbon atoms, alkoxy of 1-6 carbon atoms, cyano, halo, hydroxy, nitro, carbalkoxy of 2-7 carbon atoms, trifluoromethyl, amino, dialkylamino of 1-6 carbon atoms per alkyl group, dialkylaminoalkyl of 3-12 carbon atoms, hydroxyalkyl of 1-6 carbon atoms, alkoxyalkyl of 2-12 carbon atoms, alkylthio of 1-6 carbon atoms, —SO$_3$H, —PO$_3$H, and —CO$_2$H. It is more preferred that the aryl moiety is a phenyl group that may be optionally substituted as described above. The term alkyl of 1-6 carbon atoms includes both straight chain as well as branched carbon chains.

The chiral center(s) present in R$^1$ or R$^2$ can have either R or S configuration; this disclosure covers both enantiomers. For example when n=0, the resulting chiral carbon of the α-amino acid in the side chain of R$^1$ or R$^2$ can have either the R or S configuration, depending on the configuration of the starting material used.

Of the compounds of this invention, preferred members are those in which n=0; those in which n=0 and R$^4$ is hydrogen; those in which n=0, R$^4$ is hydrogen, and q=0; those in which n=0, R$^4$ is hydrogen, q=0, and p=1; those in which n=0, R$^4$, R$^5$, and R$^6$ are hydrogen, q=0, and p=1; and those in which n=0, R$^2$, R$^4$, R$^5$, and R$^6$ are hydrogen, q=0, and p=1.

The compounds of this invention that are esterified at the 42- or 31,42-positions can be prepared by initially acylating rapamycin with an acylating agent having the general structure

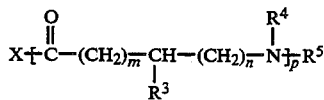

where X is OH, in the presence of a coupling reagent, such as dicyclohexylcarbodiimide or a suitably activated ester (nitrophenyl, trichlorophenyl, pentafluorophenyl, hydroxybenzotriazolyl, N-hydroxysuccinimido, and the like). The compounds of this invention also can be prepared using a carboxylic acid anhydride as the acylating species. Mixtures of 42- and 31,42-esters can be separated by chromatography.

Alternatively, the acylating species can be a mixed anhydride of the above described carboxylic acid or an acid halide, where X can be Cl, Br, or I. The acylating groups used to prepare the compounds of this invention are commercially available or can be prepared by methods that are disclosed in the literature.

The 31-esters of this invention can be prepared by protecting the 42-alcohol of rapamycin with a protecting group, such as with a tert-butyl dimethylsilyl group, followed by esteritication of the 31-position by the procedures described above. The preparation of rapamycin 42-silyl ethers is described in U.S. Pat. No. B1 5,120,842, which is hereby incorporated by reference. Removal of the protecting group provides the 31-esterified compounds. In the case of the tert-butyl dimethylsilyl protecting group, deprotection can be accomplished under mildly acidic conditions, such as acetic acid/water/THF. The deprotection procedure is described in Example 15 of U.S. Pat. No. 5,118,678, which is hereby incorporated by reference.

Having the 31-position esterified and the 42-position deprotected, the 42-position can be esterified using a different acylating agent than was reacted with the 31-alcohol, to give compounds having different esters at the 31- and 42-positions. Alternatively, the 42-esterified compounds, prepared as described above, can be reacted with a different acylating agent to provide compounds having different esters at the 31- and 42-positions.

This invention also covers analogous esters of other rapamycins such as, but not limited to, 29-demethoxyrapamycin, [U.S. Pat. No. 4,375,464, 32-demethoxyrapamycin under C.A. nomenclature]; rapamycin derivatives in which the double bonds in the 1-, 3-, and/or 5-positions have been reduced [U.S. Pat. No. 5,023,262]; 29-desmethylrapamycin [U.S. Pat. No. 5,093,339, 32-desmethylrapamycin under C.A. nomenclature]; 7,29-bisdesmethylrapamycin [U.S. Pat. No. 5,093,338, 7,32-desmethylrapamycin under C.A. nomenclature]; 27-hydroxyrapamycin [U.S. Pat. No. 5,256,790] and 15-hydroxyrapamycin [U.S. Pat. No. 5,102,876]. This invention also covers esters at the 31-position of 42-oxorapamycin [U.S. Pat. No. 5,023,263]. The disclosures in the above cited U.S. Patents are hereby incorporated by reference.

Immunosuppressive activity for representative compounds of this invention was evaluated in an in vitro standard pharmacological test procedure to measure lymphocyte proliferation (LAF) and in an in vivo standard pharmacological test procedure which evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. For each compound evaluated, rapamycin was also evaluated for the purpose of comparison. An IC$_{50}$ was obtained for each test compound as well as for rapamycin. When evaluated as a comparator for the representative compounds of this invention, rapamycin had an IC$_{50}$ ranging from 2.8 to 11.6 nM. The results obtained for the representative compounds of this invention are presented as IC$_{50s}$.

Representative compounds of this invention were also evaluated in an in vivo test procedure designed to determine the survival time of pinch skin graft from male BALB/c donors transplanted to male C3H(H-2K) recipients. The method is adapted from Billingham R. E. and Medawar P. B., J. Exp. Biol. 28:385–402, (1951). Briefly, a pinch skin graft from the donor was grafted on the dorsum of the recipient as a allograft, and an isograft was used as control in the same region. The recipients were treated with either varying concentrations of test compounds intraperitoneally or orally. Rapamycin was used as a test control. Untreated recipients serve as rejection control. The graft was monitored daily and observations were recorded until the graft became dry and formed a blackened scab. This was considered as the rejection day. The mean graft survival time (number of days ±S.D.) of the drug treatment group was compared with the control group. The following Table shows the results that were obtained. Results are expressed as the mean survival time in days. Untreated (control) pinch skin grafts are usually rejected within 6–7 days. The results shown in Table 1 are based on a dose of 4 mg/kg of test compound. A survival time of 11.67±0.63 days was obtained for rapamycin at 4 mg/kg.

The following table summarizes the results obtained with representative compounds of this invention in these two standard test procedures.

TABLE 1

EVALUATION OF INMMUNOSUPPRESSIVE ACTIVITY

| Compound | LAF $IC_{50}$ (nm) | Skin Graft (days ± SD) |
|---|---|---|
| Example 1 | 10.7 | 10.00 ± 0.00 |
| Example 3 | 2.5 | 10.17 ± 0.75 |
| Example 4 | 3.2 | 11.00 ± 1.00 |
| Example 5 | 3.9 | 10.83 ± 0.75 |
| Example 7 | 14 | 10.80 ± 0.40 |
| Example 9 | 7.8 | 11.20 ± 1.00 |
| Example 10 | 27.1 | 10.17 ± 0.41 |
| Example 11 | 1.1 | 11.50 ± 1.05 |
| No Treatment | | 7.00 ± 0.00 |

The results of these standard pharmacological test procedures demonstrate immunosuppressive activity both in vitro and in vivo for the compounds of this invention. The results obtained in the LAF test procedure show suppression of T-cell proliferation, thereby demonstrating the immunosuppressive activity of the compounds of this invention. As transplanted pinch skin grafts are typically rejected within 6-7 days without the use of an immunosuppressive agent, the increased survival time of the skin graft when treated with the compounds of this invention further demonstrates their utility as immunosuppressive agents and as agents useful for treating and preventing transplantation rejection and graft vs. host disease.

Based on the results of these standard pharmacological test procedures, the compounds of this invention are useful in the treatment or prevention of transplantation rejection such as kidney, heart, liver, lung, bone marrow, pancreas (islet cells), cornea, small bowel, and skin allografts, and heart valve xenografts; in the treatment or prevention of graft vs. host disease; in the treatment of autoimmune diseases such as lupus, rheumatoid arthritis, diabetes mellitus, myasthenia gravis, and multiple sclerosis; and diseases of inflammation such as psoriasis, dermatitis, eczema, seborrhea, inflammatory bowel disease, and eye uveitis.

Because of the activity profile obtained, the compounds of this invention also are considered to have antitumor, antifungal activities, and antiproliferative activities. The compounds of this invention therefore are also useful in treating solid tumors, T-cell leukemia/lymphoma, fungal infections, and hyperproliferative vascular diseases such as restenosis and atherosclerosis.

The compounds of this invention provide a significant advantage over rapamycin, and the acyl derivatives of rapamycin in the prior art as they are substantially more potent upon oral administration, as shown for a representative compound of this invention (compound of Example 11) in the Table below. The relative oral potency is determined by comparing the oral and i.p. $ED_{50}s$ obtained in the skin graft standard pharmacological test procedure. Briefly, the compound to be tested is evaluated at the doses of 40, 10, and 2.5 mg/kg for p.o. administration and 4, 1, and 0.25 mg/kg for i.p. administration, both administered for 6 consecutive days in the skin graft test procedure so that a dose response curve can be generated for both oral and i.p. administration. The data are subjected to a parallel line analysis and an oral and i.p. $ED_{50}$ is calculated for the compound tested, and the $ED_{50}s$ are expressed as a ratio according to the following formula:

$$\frac{ED_{50} \text{ oral administration}}{ED_{50} \text{ i.p. administration}}$$

When comparing oral potency for different compounds that have been evaluated, the lower the ratio, the greater the oral bioavailability. The oral bioavailability serves as a measure of oral potency.

TABLE 2

RELATIVE PO/IP RATIOS IN MOUSE SKIN GRAFT SURVIVAL

| Compound | Skin Graft p.o./i.p. ratio* |
|---|---|
| Example 11 | 5.6 |
| Rapamycin 42-ester with (S)-5-tert-butoxy-4-tert-butoxy carbonylamino-5-oxo-pentanoic acid (U.S. Pat. No. 5,130,307) | 188.2 |

*data obtained in cremophor

The relative potency data shown Table 2 above demonstrates that the compounds of this invention have significantly higher oral bioavailability than a structurally related rapamycin ester. The increased bioavailability of the compounds of this invention provides advantages in the formulation and administration of the compounds of this invention over the compounds of the prior art.

This invention also covers the use of the compounds of this invention administered in conjunction with one or more other immunoregulatory agents for use in inducing immunosuppression or as an antiinflammatory agent. Such other immunoregulatory agents include, but are not limited to azathioprine, corticosteroids, such as prednisone and methylprednisolone, cyclophosphamide, rapamycin, cyclosporin A, FK-506, OKT-3, and ATG. By combining the compounds of this invention with such other drugs or agents for inducing immunosuppression or treating inflammatory conditions, the lesser amounts of each of the agents are required to achieve the desired effect. The basis for such combination therapy was established by Stepkowski whose results showed that the use of a combination of rapamycin and cyclosporin A at subtherapeutic doses significantly prolonged heart allograft survival time. [Transplantation Proc. 23:507 (1991)].

As the compounds of Examples 4 and 5 were prepared via the compounds of Example 4, step B and Example 5, step B, respectively, the compounds of Example 4, step B and Example 5, step B are useful as intermediates in the preparation of biologically useful compounds.

The compounds of this invention can be administered neat or formulated with a pharmaceutical carrier to a mammal in need thereof. The pharmaceutical carrier may be solid or liquid. When formulated orally, it has been found that 0.01% Tween 80 in PHOSAL PG-50 (phospholipid concentrate with 1,2-propylene glycol, A. Nattermann & Cie. GmbH) provides an acceptable oral formulation.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellant.

Liquid pharmaceutical compositions which are sterile solutions or suspensions can be utilized by, for example, intramuscular, intraperitoneal or subcutaneous injection. Sterile solutions can also be administered intravenously. The compound can also be administered orally either in liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermiable membrane covering a reservoir containing the active ingredient with or without a carrier, or a matrix containing the active ingredient. Other occlusive devices are known in the literature.

In addition, the compounds of this invention may be employed as a solution, cream, or lotion by formulation with pharmaceutically acceptable vehicles containing 0.1–5 percent, preferably 2%, of active compound which may be administered to a fungally affected area.

The dosage requirements vary with the particular compositions employed, the route of administration, the severity of the symptoms presented and the particular subject being treated. Based on the results obtained in the standard pharmacological test procedures, projected daily dosages of active compound would be 0.1 $\mu$g/kg–100 mg/kg, preferably between 0.001–25 mg/kg, and more preferably between 0.01–5 mg/kg. Treatment will generally be initiated with small dosages less than the optimum dose of the compound. Thereafter the dosage is increased until the optimum effect under the circumstances is reached; precise dosages for oral, parenteral, nasal, or intrabronchial administration will be determined by the administering physician based on experience with the individual subject treated. Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The following examples illustrate the preparation of representative compounds of this invention.

EXAMPLE 1

Rapamycin 42-ester with (S)-3-carboxy-3-[[[phenylmethoxy]carbonyl]amino]-propanoic acid Under an atmosphere of nitrogen, a solution of rapamycin (1.06 g, 1.16 mmol) and N[(phenylmethoxy)carbonyl]-L-aspartic anhydride (0.29 g, 1.16 mmole, prepared by treatment of N-[(phenylmethoxy)carbonyl]-L-aspartic acid with dicylclohexylcarbodiimide in THF) in 21 ml of 20:1 (v/v) mixture of dichloromethane and pyridine containing a catalytic amount of 4-dimethylaminopyridine, was stirred at room temperature for 24 hours. The crude reaction mixture was absorbed on silica gel Merck-60 and prepurified by flash chromatography (using dichloromethane-methanol 9:1 as eluant). Further purification was achieved by flash chromatography (using dichloromethane-methanol 19:1 as eluant) to provide the title compound as an off-white solid.

$^1$H NMR (400 MHz, CDCl$_3$): δ1.63 (s, 3H, CH$_3$C=C), 1.73 (s, 3H, CH$_3$C=C), 3.12 (s, 3H, CH$_3$O), 3.27 (s, 3H, CH$_3$O), 3.30 (s, 3H, OCH$_3$), 5.28 (s, 2H, ArCH$_2$), 7.32 (m, 5H, ArH) MS (neg. ion FAB, m/z): 1162 [M]$^-$, 590 Anal. Calc'd for C$_{63}$H$_{90}$N$_2$O$_{18}$+0.6 CH$_2$Cl$_2$: C, 62.91; H, 7.57; N, 2.31 Found: C, 62.79; H, 7.47; N, 2.79

EXAMPLE 2

Rapamycin 42-ester with (S)-3-carboxy-3-[[[phenylmethoxy]carbonyl]amino]-propanoic acid tromethamine salt A solution of the compound of Example 1 (0.54 g, 0.46 mmole) in 50 ml of methanol was mixed with a solution of TRIS buffer (0.054 g, 0.45 mmole) in 25 ml of methanol, and the solution was concentrated to dryness in vacuo. The residue was crystallized from dichloromethane-hexane, to provide the tromethamine salt of compound of Example 1 as a white solid.

$^1$H NMR (400 MHz, DMSO-d$_6$): δ1.62 (s, 3H, C=CCH$_3$), 1.74 (s, 3H, C=CCH$_3$), 3.04 (s, 3H, OCH$_3$), 3.15 (s, 3H, OCH$_3$), 3.23 (s, 3H, OCH$_3$), 7.34 (m, 5H, ArH) $^{13}$C NMR (400 MHz, DMSO-d$_6$): δ210.4, 207.5, 198.83, 171.9, 169.2, 155.7, 98.98, 61.76 MS (neg ion FAB, m/z): 1161 [M-H]$^-$, 1027, 590 Anal. Calc'd for C$_{67}$H$_{101}$N$_3$O$_{21}$+H$_2$O: C, 61.78; H, 7.97; N, 3.23 Found: C, 61.75: H, 8.24; N, 3.57

EXAMPLE 3

Rapamycin 42-ester with (S)-3-amino-3-carboxypropanoic acid

A solution of the compound of Example 1 (0.25 g, 0.21 mmole) in 20 ml of ethyl acetate, was hydrogenated over 10% palladium-on charcoal (100 mg) at atmospheric pressure. The catalyst was filtered and the filtrate was concentrated to dryness in vacuo. The residue was purified by flash chromatography (on silica gel Merck-60 using a gradient elution from 9:1 dichloromethane-methanol to 100% methanol) to provide the title compound as a solid.

$^1$NMR (400 MHz, CDCl$_3$): δ1.64 (s, 3H, C=CCH$_3$), 1.75 (s, 3H, C=CCH$_3$), 3.15 (s, 3H, OCH$_3$), 3.32 (s, 6H, OCH$_3$) $^{13}$C NMR (400 MHz, DMSO-d$_6$): δ210.4, 209.6, 207.5, 200.9, 198.8, 169.2, 166.99, 139.3, 137.8, 137.1, 132.34, 130.42, 126.99, 124.77, 99 MS (neg ion FAB, m/z): 1027 [M-H]$^-$

EXAMPLE 4

Rapamycin 42-ester with (S)-4-carboxy-4-[[[propyloxy]carbonyl]amino]butanoic acid Step A. N-allyloxycarbonyl-L-glutamic acid-αbenzyl ester A 1N solution of NaOH (4.2 ml) was added dropwise to a stirred solution of L-glutamic acid-α-benzyl ester (1 g, 4.2 mmole) and allyl chloroformate (0.45 ml, 4.2 mmole) in 20 ml of THF. After stirring at ambient temperature for 2 hours, the reaction mixture was diluted with ether and the solution washed with water and brine. Upon drying (Na$_2$SO$_4$) the solvent was removed in vacuo and the residue recrystallized from ethyl acetate-hexane to provide the pure title compound (white needles, m.p. 81°-82.5° C.).

$^1$NMR (400 MHz, CDCl$_3$): δ1.99 (m, 1H, CCH$_2$C), 2.22 (m, 1H, CCH$_2$C), 2.44 (m, 2H, CCH$_2$COO), 4.46 [m, 1H, CCH(NH)COO], 4.56 (d, 2H, OCH$_2$CH=), 5.17 (s, 2H, OCH$_2$Ar), 5.19-5.31 (m, 2H, CC=CH$_2$), 5.45 (m, 1H, NH), 5.88 (m, 1H, CCH=C), 7.347 (m, 5H, ArH) MS (EI, m/z): 321 [M]$^+$, 186 (b.p.) [α]$_D^{25}$= −26.63 (methanol, c=10.061) Anal calc'd for C$_{16}$H$_{19}$NO$_6$: C, 59.81; H, 5.96; N, 4.36 Found : C, 59.89; H, 5.63; N, 4.34

Step B. Rapamycin 42-ester with (S)-5-phenylmethoxy-4-[[[allyloxy]carbonyl]amino]-5-oxopentanoic acid Under anhydrous conditions, an ice cold solution of rapamycin (1.37 g, 1.5 mmole) and N-allyloxycarbonyl-L-glutamic acid-α-benzyl ester (0.5 g, 1.56 mmole, from Example 4, Step A) in 25 ml of dry dichloromethane was treated with dicyclohexylcarbodiimide (0.33 g, 1.6 mmole), followed by 4-dimethylamino pyridine (0.20 g, 1.6 mmole). After stirring overnight at ambient temperature, the solids were filtered and washed with dichloromethane. The filtrate was preabsorbed on Merck silica gel 60 and purified by flash chromatography (dichloromethane-ethyl acetate 2:1), to give the title compound as a white solid.

$^1$H NMR (400 MHz, CDCl$_3$): δ1.65 (s, 3H, C=CCH$_3$), 1.75 (s, 3H, C=CCH$_3$), 3.13 (s, 3H, OCH$_3$), 3.33 (m, 6H, CH$_3$O), 4.56 (d, 2H, CH$_2$C=C), 5.17 (s, 2H, CH$_2$Ar), 7.35 (m, 5H, ArH) MS (neg ion FAB, m/z): 1216 [M]$^-$, 1125, 590, 476.3 Anal calc'd for C$_{67}$H$_{96}$N$_2$O$_{18}$: C, 66.10; H, 7.95; N, 2.30 Found C, 65.76; H, 8.07; N, 2.42

Step C. Rapamycin 42-ester with (S)-4-carboxy-4-[[[propyloxy]carbonyl]amino]-butanoic acid A mixture of rapamycin 42-ester of Example 4, Step B (0.270 g, 0.22 mmole), fresh 1,4-cyclohexadiene (0.178 ml, 2.2 mmole) and 0.25 g of 10% palladium on carbon in 50 ml of absolute ethanol, were stirred at ambient temperature for 4 hours. The catalyst was filtered (Solka Floc) and the filtrate is concentrated in vacuo to give a white foam. The residue was purified by flash chromatography (on silica Merck-60, dichloromethane-methanol 9:1) to provide the title compound as a white solid.

$^1$H NMR (400 MHz, DMSO-d$_6$): δ1.615 (s, 3H, CH$_3$C=C), 1.739 (s, 3H, CH$_3$C=C), 3.036 (s, 3H, CH$_3$O), 3.14 (s, 3H, CH$_3$O), 3.25 (s, 3H, CH$_3$O), 3.857 (m, 2H, OCH$_2$CH$_2$) $^{13}$C NMR (400 MHz, DMSO-d$_6$): δ210.38, 207.57, 198.85, 172.39, 169.24, 167.01, 155.78, 139.31, 137.88, 137.16, 132.36, 130.44, 127.02, 124.77, 99.03 MS (neg ion FAB, m/z): 1127 [M-H]$^-$

EXAMPLE 5

Rapamycin 42-ester with (R)-4-carboxy-4[[[propyloxy]-carbonyl]amino]butanoic acid Step A. N-allyloxycarbonyl-D-glutamic acid-α-benzyl ester A 1N solution of NaOH was added dropwise to a stirred solution of D-glutamic acid-α-benzyl ester (3.5 g, 14.7 mmole) and allylchloroformate (1.56 ml. 14.7 mmole) in 25 ml of THF. After stirring at ambient temperature for 2 hours, the reaction mixture was diluted with ether and washed with water and brine. Upon drying (Na$_2$SO$_4$) the solvent was removed in vacuo and the residue recrystallized from ethyl acetate-hexane to provide pure title compound (white needles, m.p. 81°-82.5° C.).

$^1H$ NMR (400 MHz, CDCl$_3$): δ1.98 (m, 1H, CCH$_2$C), 2.206 (m, 1H, CCH$_2$C), 2.43 (m, 2H, CCH$_2$COO), 4.45 [m, 1H, CCH(NH)COO], 4.54 (d, 2H, OCH$_2$C=), 5.16 (s, 2H, OCH$_2$Ar), 5.18-5.30 (m, 2H, CC=CH$_2$), 5.40 (m, 1H, CCH=C), 7.335 (m, 5H, ArH) MS (EI, m/z): 321 [M]$^+$, 186 (bp) [α]$_D^{25}$= +27.107 (methanol, c=10) Anal. calc'd for C$_{16}$H$_{29}$NO$_6$: C, 59.81; H, 5.96; N, 4.36 Found: C, 59.82; H, 5.68; N, 4.30

Step B. Rapamycin 42-ester with (R)-5-phenylmethoxy-4-[[[allyloxy]carbonyl]amino]-5-oxopentanoic acid Under anhydrous conditions, an ice cold solution of rapamycin (4.3 g, 4.7 mmole) and N-allyloxycarbonyl-D-glutamic acid-α-benzyl ester (1.6 g, 5 mmole) (Example 5, Step A) in dry dichloromethane (50 ml) was treated with dicylclohexylcarbodiimide (1 g, 5 mmole) followed by 4-dimethylamino pyridine (0.61 g, 5 mmole). After stirring overnight at room temperature, the solids were filtered and washed with dichloromethane. The filtrate was preabsorbed on silica gel Merck 60 and flash chromatographed (hexane-ethyl acetate gradient elution from 2:1 to 3:2) to give the title compound as a white solid.

$^1$H NMR (400 MHz, CDCl$_3$): δ1.65 (s, 3H, C═CCH$_3$), 1.748 (s, 3H, C═CCH$_3$), 3.138 (s, 3H, CH$_3$O), 3.33 (m, 6H, CHO), 4.56 (d, 2H, CH$_2$C═C), 5.17 (s, 2H, CH$_2$Ar), 7.35 (m, 5H, ArH) MS (neg. ion FAB, m/z): 1216 [M]$^-$, 1125, 1067, 624, 590 Anal calc'd for C$_{67}$H$_{92}$N$_2$O$_{18}$·0.5 C$_4$H$_8$O$_2$: C, 65.69; H, 7.99; N, 2.22 Found: C, 65.37; H, 8.02; N, 2.14

Step C. Rapamycin 42-ester with (R)-4-carboxy-4[[[propyloxy]carbonyl]amino]-butanoic acid A mixture of the compound of Example 5, Step B (1.98 g, 1,5 mmole), fresh 1,4-cyclohexadiene (1.4 ml, 15 mmole) and 10% Pd on carbon (1.9 g) in 50 ml of absolute ethanol, were stirred at ambient temperature for 4 hours. The catalyst was filtered (Solka-Floc) and the filtrate concentrated in vacuo to give a white foam. Flash chromatography of the crude mixture ( on silica Merck 60, dichloromethane-methanol 9:1) provided the title compound as a white solid.

$^1$H NMR (400 MHz, DMSO-d$_6$): δ1.614 (s, 3H, C═CCH$_3$), 1.739(s, 3H, C═CCH$_3$), 3.037 (s, 3H, CH$_3$O), 3.14 (m, 3H, CH$_3$O), 3.24 (s, 3H, CH$_3$O), 3.857 (m, 2H, OCH$_2$CH$_2$). MS (neg. ion FAB, m/z): 1127 [M]$^-$ Anal calc'd for C$_{60}$H$_{92}$N$_2$O$_{18}$·0.6 CH$_2$Cl$_2$: C, 61.67; H, 7.96; N, 2.37 Found C. 61.31; H, 7.82; N, 2.35

EXAMPLE 6

Rapamycin 42-ester with (R)-4-carboxy-4-[[[propyloxy]carbonyl]amino]butanoic acid tromethamine salt A solution of the compound of Example 5. Step C (0.30 g, 0.27 mmole) in 5 ml of methanol was mixed with a solution of tris(hydroxymethyl)aminomethane (0.032 g, 0.27 mmole) in 5 ml of methanol. The clear solution was concentrated to about 3 ml and diluted with diethylether until persistent turbidity was observed. The solid that crystallized over a period of time was collected and dried.

$^1$H NMR (400 MHz, DMSO-d$_6$): δ1.615 (s, 3H, C═CCH$_3$), 1.738 (s, 3H, C═CCH$_3$), 3.036 (s, 3H, CH$_3$O), 3.143 (m, 3H, CH$_3$O), 3.23 (s, 3H, CH$_3$O), 3.322 (s, 6H, CH$_2$O), 3.857 (m, 2H, OCH$_2$CH$_2$). MS (neg. ion FAB, m/z): 1127 [M]$^-$

EXAMPLE 7

Rapamycin 42-ester with (S)-4-amino-4-carboxybutanoic

Step A. Rapamycin 42-ester with (S)-5-phenylmethoxy-4-[[[phenylmethoxy]carbonyl]amino]-5-oxo-pentanoic acid Under an atmosphere of nitrogen, a solution of rapamycin (4.3 g, 4.7 mmole), N$^α$-(benzyloxycarbonyl)-L-glutamic acid α-benzyl ester (1.86 g, 5 mmole), dicyclohexylcarbodiimide (1 g, 5 mmole) and 4-dimethylaminopyridine (0,61 g, 5 mmole) in 10 ml of dichloromethane were stirred at ambient temperature for 72 hours. The crude reaction mixture was preabsorbed on silica gel Merck 60 and flash chromatographed (using ethyl acetate-hexane 3:1 as the eluant) to provide the title compound as a white solid.

$^1$H NMR (400 MHz, CDCl$_3$): δ1.654 (s, 3H, C═CCH$_3$), 1.75 (s, 3H, C═CCH$_3$), 3.138 (s, 3H, CH$_3$O), 3.195 (m, 3H, CH$_3$O), 3.325 (s, 3H, CH$_3$O), 5.102 (s, 2H, CH$_2$Ar), 5.172 (s, 2H CH$_2$Ar), 7.34 (s, 10H, ArH) MS (neg. ion FAB, m/z): 1266 [M]$^-$, 1175.5, 590 [α]$_D^{25}$=−106.4 (methanol, c=10.15) Anal. calc'd. for C$_{71}$H$_{98}$N$_2$O$_{18}$+0.5 C$_4$H$_8$O$_2$: C, 66.51; H, 7.80; N, 2.12 Found: C, 66.57; H, 7.80; N, 2.28

Step B. Rapamycin 42-ester with (S)-4-amino-4-carboxy-butanoic acid

To a stirred mixture of compound of Example 7, Step A (1.4 g, 1.1 mmole) and 10% Pd on carbon (1.2 g) in 60 ml of methanol was added ammonium formate (0.35 g, 5,5 mmole) in one portion. After 15 min the catalyst was filtered (Solka Floc) and the filtrate concentrated in vacuo. The residue was triturated with water, the solid collected and dried in vacuo to give fairly pure title compound. Further purification was achieved by HPLC (C18-Dynamax 60A 41×250 mm column, A=H$_2$O, B=CH$_3$CN, gradient elution from 40% to 90% B, flow rate 20 ml/min).

$^1$H NMR (400 MHz, CDCl$_3$): δ1.623 (s, 3H, C═CCH$_3$), 1.743 (s, 3H, C═CCH$_3$), 3.044 (s, 3H, CH$_3$O), 3.152 (m, 3H, CH$_3$O), 3.287 (s, 3H, CH$_3$O), 4.52 (m, 1H, 42-H) $^{13}$C NMR (400 MHz, CDCl$_3$): δ210.38, 207.52, 198.8, 171.96, 169.19, 169.11, 166.99, 139.29, 137.83, 137.13, 132.33, 130.39, 126.99, 124.79. 98.99 MS (neg. ion FAB, m/z): 1041 [M-H]$^-$, 590

EXAMPLE 8

Rapamycin 42-ester with (S)-4-amino-4-carboxybutanoic acid maleate salt

A solution of the compound of Example 7, Step B (0.25 g, 0.24 mmole) in 10 ml of dichloromethane was mixed with a solution of maleic acid (0.035 g, 0.03 mmole) in 2 ml of methanol. The solvents were evaporated and the residue was triturated with diethylether to provide the title compound as a white solid.

$^1$H NMR (400 MHz, CDCl$_3$): δ1.616 (s, 3H, C═CCH$_3$), 1.743 (s, 3H, C═CCH$_3$), 3.038 (s, 3H, CH$_3$O), 3.145 (m, 3H, CH$_3$O), 3.258 (s, 3H, CH$_3$O), 6.08 (s, 2H, C═CHCOO), 8.2 (broad, 3H, NH$_3^+$) MS (neg. ion FAB, m/z): 1041 [M-H]$^-$

EXAMPLE 9

Rapamycin 42-ester with (R)-4-amino-4-carboxybutanoic acid

Step A. Rapamycin 42-ester with (R)-5-phenylmethoxy-4-[[[phenylmethoxy]carbonyl]amino]-5-oxo-pentanoic acid Under a nitrogen atmosphere a solution of rapamycin (4.3 g, 4.7 mmole), N-benzyloxycarbonyl-D-glutamic acid α-benzyl ester (1.86 g, 5 mmole), dicyclohexylcarbodiimide (1 g, 5 mmole) and 4-dimethylaminopyridine (0.61 g, 5 mmole) in 10 ml of dichloromethane were stirred at room temperature for 72 hours. The crude reaction mixture was preabsorbed on silica gel Merck 60 and flash chromatographed (using ethyl acetate-hexane 3:1 as the eluant) to provide the title compound as a white solid.

$^1$H NMR (400 MHz, CDCl$_3$): δ1.654 (s, 3H, CH$_3$), 1.751 (s, 3H, CH$_3$C═C), 3.138 (s, 3H, CH$_3$O), 3.18 (s, 3H, CH$_3$O), 3.33 (d, 1H, 31-CH), 5.10 (s, 2H, CH$_2$Ar), 5.176 (s, 2H, CH$_2$Ar), 7.346 (s, 10 H, ArH) MS (neg. ion FAB, m/z): 1266 [M]⁻, 1175.5, 1067.4, 590 [α]$_D^{25}$ = −90.6 (methanol, c=10) Anal. calc'd. for C$_{71}$H$_{98}$N$_2$O$_{18}$: C, 67.28; H, 7.79; N, 2.21 Found: C, 67.08; H, 7.88; N, 2.33

Step B. Rapamycin 42-ester with (R)-4-amino-4-carboxy-butanoic acid

To a stirred mixture of the rapamycin 42-ester of Example 9, Step A (1.5 g, 1.18 mmole) and 1.2 g of 10% Pd on carbon in 60 ml of methanol was added ammonium formate (0.37 g, 5.9 mmole) in one portion. After 15 minutes, the catalyst was filtered off (Solka Floc) and the filtrate concentrated in vacuo to give fairly pure title compound. Further purification was achieved by HPLC [on a Dynamax 60A C$_{18}$ 41×250 mm column using a gradient elution 40-90% B (A=H$_2$O, B=CH$_3$CN), 20 ml/min flow rate] to provide the title compound as a white solid.

$^1$H NMR (400 MHz, CDCl$_3$): δ1.616 (s, 3H, C═CCH$_3$), 1.739 (s, 3H, C═CCH$_3$), 3.038 (s, 3H, CH$_3$O), 3.146 (m, 3H, CH$_3$O), 3.263 (s, 3H, CH$_3$O), 4.5 (m, 1H, 42-H) $^{13}$C NMR (400 MHz, CDCl$_3$): δ210.38, 207.57, 198.86, 171.98, 169.19, 169.23, 169.12, 167, 139.32, 137.87, 137.16, 132.36, 130.43, 127.02. 124.77, 99.02 MS (neg. ion FAB, m/z): 1041 [M-H]⁻, 590 Anal. calc'd for C$_{56}$H$_{86}$N$_2$O$_{16}$+H$_2$O: C, 63.38; H, 8.36; N, 2.64 Found: C, 63.59; H, 8.49; N, 2.62

EXAMPLE 10

Rapamycin 42-ester with (S)-4-carboxy-4-[[[phenylmethoxy-carbonyl]-amino]-butanoic acid A solution of rapamycin (1.8 g, 2 mmole), N-benzyloxycarbonyl-L-glutamic anhydride (0.92 g, 3.5 mmole) and pyridine (1 ml) in 20 ml of dry THF containing a catalytic amount of 4-dimethylamino pyridine, was stirred overnight at ambient temperature. The solvents were removed in vacuo and the crude mixture was flash chromatographed (on silica gel Merck-60, using dichloromethane-methanol 19:1 as eluant) to provide a mixture of desired product and unreacted rapamycin. Pure title compound was obtained by HPLC (Dynamax 60A 10×250 mm C18 column, solvent system: acetonitrile-water 4:1 containing 0.1% acetic acid, flow rate 4 ml/min, UV detector at 280 nm) as a white solid.

$^1$H NMR (400 MHz, CDCl$_3$): δ1.654 (s, 3H, C═CCH$_3$), 1.75 (s, 3H, C═CCH$_3$), 3.13 (s, 3H, CH$_3$O), 3.33 (m, 6H, CH$_3$O), 5.11 (s, 2H, CH$_2$Ph), 7.35 (m, 5H, ArH). MS (neg. ion FAB, m/z): 1175 [M-H]⁻, 1041, 590

EXAMPLE 11

Rapamycin 42-ester-(S)-4-amino,5-(1,1-dimethylethoxy)-5-oxopentanoic acid

Step A. Rapamycin 42-ester with (S)-5-(1,1-dimethylethoxy),4-[[[9H-fluoren-9-ylmethoxy]carbonyl]amino]-5-oxo-pentanoic acid Under a nitrogen atmosphere, a solution of 5-(1,1-dimethylethoxy)-4-[[[6H-fluoren-9-ylmethoxy)carbonyl]amino]5-oxo-pentanoic acid (0.277 g, 0.65 mmole) in 1 ml of dry THF was treated with triethylamine (90 μl, 0.65 mmole) followed by a solution of 2.4.6-trichlorobenzoyl chloride (0.0158 g, 0.65 mmole) in 1 ml of dry THF. The reaction mixture was stirred at room temperature for 30 rain and filtered. The filtrate was added dropwise to a stirred solution of rapamycin (0.5 g, 0.54 mmole) and 4-dimethylamino pyridine (0.08 g, 0.65 mmole) in 2 ml of dry THF. After stirring overnight, the precipitate was filtered off and the filtrate was preabsorbed on silica gel Merck 60 and flash chromatographed (using an hexane-ethyl acetate gradient from 2:1 to 3:2 v/v) to provide the title compound as a white solid.

$^1$H NMR (400 MHz, CDCl$_3$): δ1.476 (s, 9H, COO-Bu$^t$), 3.13 (s, 3H, OCH$_3$), 3.32 (s, 3H, CH$_3$O), 3.40 (s, 3H, CH$_3$O), 4.22 (d, 1H, 31-CH), 4.67 (m, 1H, 42-CH), 7.31 (t, 2H, ArH), 7.39 (t, 2H, ArH), 7.63 (d, 2H, ArH, 7.76 (d, 2H, ArH) MS (neg. ion FAB, m/z): 1320 [M]⁻, 1097, 590

Step B. Rapamycin 42-ester with-(S)-4-amino-5-(1,1-dimethylethoxy)-5-oxo-pentanoic acid A solution of the rapamycin 42-ester of Example 11 Step A (1.25 g, 0.95 mmole), piperidine (93 μL, 0.95 mmole) and DMF (250 μl) in 10 ml of dry dichloromethane, was stirred at room temperature for 48 hours. The solvents were evaporated in vacuo and the crude product mixture was flash chromatographed (on silica Merck 60, with ethyl acetate as eluant) to provide the title compound as a white solid.

$^1$H NMR (400 MHz, CDCl$_3$): δ1.479 (s, 9H, COO-Bu$^t$), 1.655 (s, 3H, C═CCH$_3$), 1.766 (s, 3H, C═CCH$_3$), 3.139 (s, 3H, CH$_3$O, 3.342 (m, 3H, CH$_3$O), 3.384 (s, 3H, CH$_3$O) $^{13}$C NMR (400 MHz, CDCl$_3$): δ215.17, 208.07, 172.54, 169.27, 166.69, 139.94, 135.89, 133.44, 133.33, 130.22, 129.29, 126.62, 126.50, 126.40, 98.46 MS (neg. ion FAB, m/z): 1098[M]⁻

What is claimed is:

1. A compound of the structure

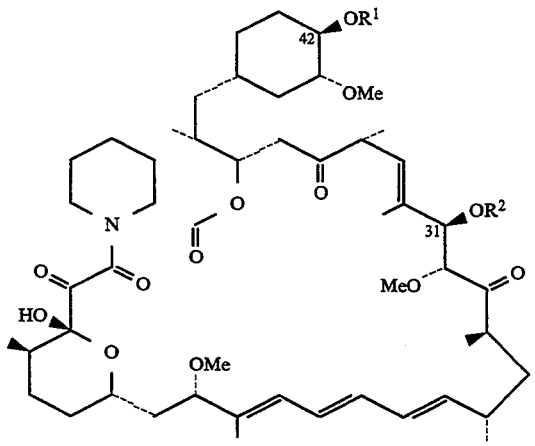

wherein R$^1$ and R$^2$ are each, independently, hydrogen or

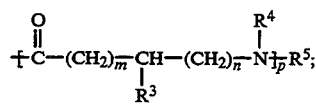

R$^3$ is —(CH$_2$)$_q$CO$_2$R$^6$;

R$^4$ is hydrogen, alkyl of 1–6 carbon atoms, or arylalkyl of 7–10 carbon atoms;

R$^5$ is hydrogen;

R$^6$ is hydrogen, alkyl of 1–6 carbon atoms, alkenyl of 2–7 carbon atoms, arylalkyl of 7–10 carbon atoms, fluorenylmethyl, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or —CO₂H;

R⁷ is alkyl of 1–6 carbon atoms, alkenyl of 2–7 carbon atoms, arylalkyl of 7–10 carbon atoms, fluorenylmethyl, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or —CO₂H;

m is 0–4;
n is 0–4;
p is 1–2;
q is 0–4;
wherein $R^3$, $R^4$, m, and n are independent in each of the

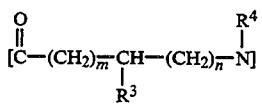

subunits when p=2;
with the proviso that $R^1$ and $R^2$ are not both hydrogen; and further provided that if $R^5$ is $CO_2R^7$, then $R^6$ is hydrogen; and still further provided that if $R^6$ is not hydrogen, then $R^5$ is hydrogen;
or a pharmaceutically acceptable salt thereof.

2. The compound according to claim 1 wherein n=0 or a pharmaceutically acceptable salt thereof.

3. The compound according to claim 2 wherein $R^4$ is hydrogen or a pharmaceutically acceptable salt thereof.

4. The compound according to claim 3 wherein q=0 or a pharmaceutically acceptable salt thereof.

5. The compound according to claim 4 wherein p=1 or a pharmaceutically acceptable salt thereof.

6. The compound according to claim 5 wherein $R^2$ is hydrogen or a pharmaceutically acceptable salt thereof.

7. The compound according to claim 1 which is rapamycin 42-ester with (S)-3-amino-3-carboxypropanoic acid or a pharmaceutically acceptable salt thereof.

8. The compound according to claim 1 which is rapamycin 42-ester with (S)-4-amino-4-carboxybutanoic acid or a pharmaceutically acceptable salt thereof.

9. The compound according to claim 1 which is rapamycin 42-ester with (S)-4-amino-4-carboxybutanoic acid maleate salt.

10. The compound according to claim 1 which is rapamycin 42-ester with (R)-4-amino-4-carboxybutanoic acid or a pharmaceutically acceptable salt thereof.

11. The compound according to claim 1 which is rapamycin 42-ester with (S)-4-amino-5-(1,1-dimethylethoxy)-5-oxopentanoic acid or a pharmaceutically acceptable salt thereof.

12. A method of inducing immunosuppression in a mammal in need thereof which comprises, administering to said mammal an immunosuppressive amount of a compound of the structure

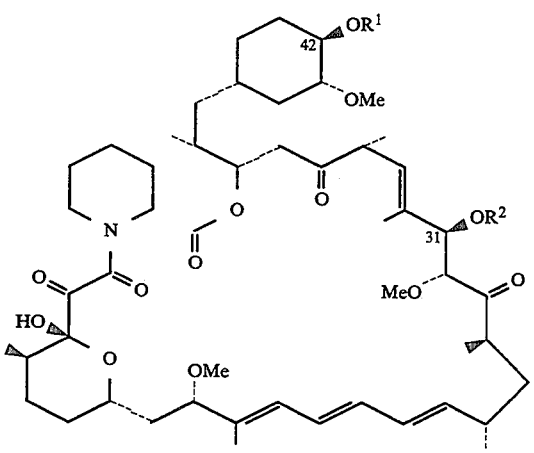

wherein $R^1$ and $R^2$ are each, independently, hydrogen or

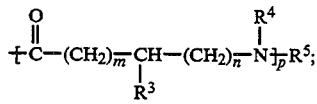

$R^3$ is $-(CH_2)_qCO_2R_6$;
$R^4$ is hydrogen, alkyl of 1–6 carbon atoms, or arylalkyl of 7–10 carbon atoms;
$R^5$ is hydrogen;
$R^6$ is hydrogen, alkyl of 1–6 carbon atoms, alkenyl of 2–7 carbon atoms, arylalkyl of 7–10 carbon atoms, fluorenylmethyl, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or —CO₂H;
R⁷ is alkyl of 1–6 carbon atoms, alkenyl of 2–7 carbon atoms, arylalkyl of 7–10 carbon atoms, fluorenylmethyl, or phenyl which is optionally mono-, di-, or tri-substituted with a substituent selected from alkyl of 1–6 carbon atoms, alkoxy of 1–6 carbon atoms, hydroxy, cyano, halo, nitro, carbalkoxy of 2–7 carbon atoms, trifluoromethyl, amino, or —CO₂H;
m is 0–4;
n is 0–4;
p is 1–2;
q is 0–4;
wherein $R^3$, $R^4$, m, and n are independent in each of the

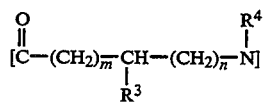

subunits when p=2;
with the proviso that $R^1$ and $R^2$ are not both hydrogen; and further provided that if $R^5$ is $CO_2R^7$, then $R^6$ is hydrogen; and still further provided that if $R^6$ is not hydrogen, then $R^5$ is hydrogen;
or a pharmaceutically acceptable salt thereof.

13. The method according to claim 12 wherein the induced immunosuppression is used to prevent or treat transplantation rejection or graft versus host disease.

14. A pharmaceutical composition which comprises an effective amount of a compound of the structure

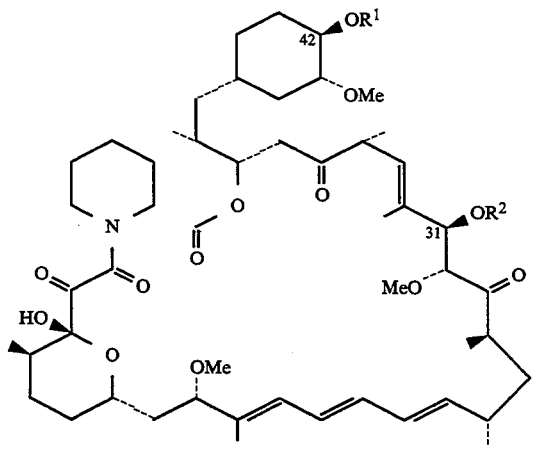

wherein $R^1$ and $R^2$ are each, independently, hydrogen or

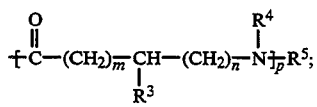

$R^3$ is $-(CH_2)_q CO_2 R^6$;

$R^4$ is hydrogen, alkyl of 1-6 carbon atoms, or arylalkyl of 7-10 carbon atoms;

$R^5$ is hydrogen;

$R^6$ is hydrogen, alkyl of 1-6 carbon atoms, alkenyl of 2-7 carbon atoms, arylalkyl of 7-10 carbon atoms, fluorenylmethyl, or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or $-CO_2H$;

$R^7$ is alkyl of 1-6 carbon atoms, alkenyl of 2-7 carbon atoms, arylalkyl of 7-10 carbon atoms, fluorenylmethyl, or phenyl which is optionally mono-, di-, or tri-substituted with a substituent selected from alkyl of 1-6 carbon atoms, alkoxy of 1-6 carbon atoms, hydroxy, cyano, halo, nitro, carbalkoxy of 2-7 carbon atoms, trifluoromethyl, amino, or $-CO_2H$;

m is 0-4;
n is 0-4;
p is 1-2;
q is 0-4;

wherein $R^3$, $R^4$, m, and n are independent in each of the

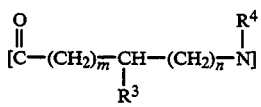

subunits when p=2;

with the proviso that $R^1$ and $R^2$ are not both hydrogen; and further provided that if $R^5$ is $CO_2R^7$, then $R^6$ is hydrogen; and still further provided that if $R^6$ is not hydrogen, then $R^5$ is hydrogen;

or a pharmaceutically acceptable salt thereof and a pharmaceutical carrier.

* * * * *